US010954292B2

(12) United States Patent
Patel et al.

(10) Patent No.: US 10,954,292 B2
(45) Date of Patent: *Mar. 23, 2021

(54) ANTI-PACAP ANTIBODY

(71) Applicant: Eli Lilly and Company, Indianapolis, IN (US)

(72) Inventors: Chetankumar Natvarlal Patel, Fishers, IN (US); Michael Parvin Johnson, Carmel, IN (US); Catherine Brautigam Beidler, Poway, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/692,236

(22) Filed: Nov. 22, 2019

(65) Prior Publication Data

US 2020/0131256 A1 Apr. 30, 2020

Related U.S. Application Data

(63) Continuation of application No. 16/136,490, filed on Sep. 20, 2018, now Pat. No. 10,519,225.

(60) Provisional application No. 62/565,278, filed on Sep. 29, 2017.

(51) Int. Cl.
| | |
|---|---|
| *A61K 39/00* | (2006.01) |
| *A61K 39/395* | (2006.01) |
| *C07K 16/18* | (2006.01) |
| *A61P 29/00* | (2006.01) |
| *A61P 25/06* | (2006.01) |
| *A61K 38/00* | (2006.01) |
| *A61K 38/17* | (2006.01) |

(52) U.S. Cl.
CPC .............. *C07K 16/18* (2013.01); *A61P 25/06* (2018.01); *A61P 29/00* (2018.01); *A61K 38/005* (2013.01); *A61K 38/1796* (2013.01); *A61K 2039/505* (2013.01); *C07K 2317/24* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,486,472 | A | 1/1996 | Suzuki et al. |
| 6,037,321 | A | 3/2000 | Cox et al. |
| 2016/0027984 | A1 | 1/2016 | Shiraishi et al. |
| 2016/0304604 | A1 | 10/2016 | Loomis et al. |

FOREIGN PATENT DOCUMENTS

| | | |
|---|---|---|
| WO | 1991/014786 A1 | 10/1991 |
| WO | 2003/005311 A2 | 6/2004 |
| WO | 2004/062684 A2 | 7/2004 |
| WO | 2012/106407 A2 | 8/2012 |
| WO | 2015/023890 A1 | 2/2015 |
| WO | 2016/168757 A1 | 10/2016 |
| WO | 2016/168760 A1 | 10/2016 |
| WO | 2016/168762 A3 | 10/2016 |
| WO | 2016/168768 A2 | 10/2016 |
| WO | 2017/106578 A1 | 6/2017 |
| WO | 2017/142961 A1 | 8/2017 |

OTHER PUBLICATIONS

Schytz et al., The PACAP receptor: a novel target for migraine treatment.Neurotherapeutics. Apr. 2010;7(2): 191-6. doi: 10.1016/j.nurt.2010.02.003 (Year: 2010).*
Kabat, et al., Attempts to locate complementarity-determining residues in the variable positions of light and heavy chains, Ann. NY Acad. Sci. 190:382-93 (1971).
North et al., A New Clustering of Antibody CDR Loop Conformations, Journal of Molecular Biology, 406:228-256 (2011).
A Miyata, Biochem Biophys Res Commun 170: 643-648 (1990) "Isolation of a neuropeptide corresponding to the N-terminal 27 residues of the pituitary adenylate cyclase activating polypeptide with 38 residues (PACAP38)."
Estep et al, mAbs, 2013. 5:270-278 "High throughput solution-based measurement of antibody-antigen affinity and epitope binning".
Schytz, et al, "The PACAP Receptor: A novel target for migraine treatment" Neurotherapeutics, vol. 7, No. 2, 2010.
Zagami, et al, "Pituitary adenylate cyclase activating polypeptide and migraine". ANNALS of Clinical and Translational Neurology. 2014; 1(12): 1036-1040.
Schwarzhoff et al. "Specific monoclonal antibodies neutralize the action of PACAP 1-27 or PACAP 1-38 on intestinal muscle strips in vitro". Regulatory Peptides 55 (1995) 57-66.
Rainer Schwarzhoff et al: "Specific monoclonal antibodies neutralize the action of PACAP 1-27 or PACAP 1-38 on intestinal muscle strips in vitro". Regulatory Peptides, vol. 55 , No. 1, Jan. 1, 1995 (Jan. 1, 1995), pp. 57-66.
Alessandro S. Zagami et al: "Pituitary adenylate cyclase activating polypeptide and migraine", Annals of Clinical and Translational Neurology, vol. 1, No. 12, Nov. 12, 2014 (Nov. 12, 2014), pp. 1036-1040.
H. W. Schytz et al: "PACAP38 induces migraine-like attacks in patients with migraine without aura", Brain., vol. 132, No. 1, Nov. 11, 2008 (Nov. 11, 2008), pp. 16-25.
D. Vaudry et al: "Pituitary Adenylate Cyclase-Activating Polypeptide and Its Receptors: 20 Years after the Discovery", Pharmacological Reviews, vol. 61, No. 3, Sep. 1, 2009 (Sep. 1, 2009), pp. 283-357.

* cited by examiner

*Primary Examiner* — Aurora M Fontainhas
(74) *Attorney, Agent, or Firm* — Duane C. Marks

(57) ABSTRACT

Antibodies to human pituitary adenylate cyclase-activating peptide, compositions comprising such antibodies, and methods of using such antibodies for the treatment of pain including headache and/or migraine.

18 Claims, No Drawings

Specification includes a Sequence Listing.

SEQUENCE LISTING

```
<160> NUMBER OF SEQ ID NOS: 14

<210> SEQ ID NO 1
<211> LENGTH: 449
<212> TYPE: PRT
<213> ORGANISM: Artificial Sequence
<220> FEATURE:
<223> OTHER INFORMATION: Exemplified HC
<220> FEATURE:
<221> NAME/KEY: MISC_FEATURE
<222> LOCATION: (62)..(62)
<223> OTHER INFORMATION: Xaa at residue 62 is one of Asp, Ala, Glu, and
      Gln
<220> FEATURE:
<221> NAME/KEY: MISC_FEATURE
<222> LOCATION: (104)..(104)
<223> OTHER INFORMATION: Xaa at residue 104 is one of Asn and Thr
<220> FEATURE:
<221> NAME/KEY: MISC_FEATURE
<222> LOCATION: (231)..(231)
<223> OTHER INFORMATION: Xaa at residue 231 is one of Pro and Ser
<220> FEATURE:
<221> NAME/KEY: MISC_FEATURE
<222> LOCATION: (237)..(237)
<223> OTHER INFORMATION: Xaa at residue 237 is one of Ala and Phe
<220> FEATURE:
<221> NAME/KEY: MISC_FEATURE
<222> LOCATION: (238)..(238)
<223> OTHER INFORMATION: Xaa at residue 238 is one of Ala and Leu

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Leu Ser Gly Gly Ser Thr Tyr Tyr Ala Xaa Ser His
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Val Gly Ala Ser Xaa His Asn Tyr Tyr Gly Met Asp Val
            100                 105                 110

Trp Gly Gln Gly Thr Met Val Thr Val Ser Ser Ala Ser Thr Lys Gly
```

```
            115                 120                 125
Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
        210                 215                 220

Tyr Gly Pro Pro Cys Pro Xaa Cys Pro Ala Pro Glu Xaa Xaa Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly

<210> SEQ ID NO 2
<211> LENGTH: 214
<212> TYPE: PRT
<213> ORGANISM: Artificial Sequence
<220> FEATURE:
<223> OTHER INFORMATION: Exemplified LC
<220> FEATURE:
<221> NAME/KEY: MISC_FEATURE
<222> LOCATION: (30)..(30)
<223> OTHER INFORMATION: Xaa at residue 30 is one of Ser and Trp
<220> FEATURE:
<221> NAME/KEY: MISC_FEATURE
<222> LOCATION: (55)..(55)
<223> OTHER INFORMATION: Xaa at residue 55 is one of Leu and Phe
```

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Xaa Arg Trp
            20                  25                  30

Leu Ala Trp Tyr Gln Gln Lys Pro Gly Lys Ala Pro Lys Leu Leu Ile
        35                  40                  45

His Asp Ala Ser Gln Leu Xaa Glu Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asp Leu Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 13
<212> TYPE: PRT
<213> ORGANISM: Artificial Sequence
<220> FEATURE:
<223> OTHER INFORMATION: Exemplified HCDR1

<400> SEQUENCE: 3

Ala Ala Ser Gly Phe Thr Phe Ser Ser Tyr Tyr Met Ser
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Exemplified HCDR2
<220> FEATURE:
<221> NAME/KEY: MISC_FEATURE
<222> LOCATION: (13)..(13)
<223> OTHER INFORMATION: Xaa at residue 13 is one of Asp, Ala, Glu and
      Gln

<400> SEQUENCE: 4

Ala Ile Ser Leu Ser Gly Gly Ser Thr Tyr Tyr Ala Xaa Ser His Lys
1               5                   10                  15

Gly

```
<210> SEQ ID NO 5
<211> LENGTH: 16
<212> TYPE: PRT
<213> ORGANISM: Artificial Sequence
<220> FEATURE:
<223> OTHER INFORMATION: Exemplified HCDR3
<220> FEATURE:
<221> NAME/KEY: MISC_FEATURE
<222> LOCATION: (8)..(8)
<223> OTHER INFORMATION: Xaa at residue 8 is one of Asn and Thr

<400> SEQUENCE: 5

Val Arg Glu Val Gly Ala Ser Xaa His Asn Tyr Tyr Gly Met Asp Val
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Exemplified LCDR1
<220> FEATURE:
<221> NAME/KEY: MISC_FEATURE
<222> LOCATION: (7)..(7)
<223> OTHER INFORMATION: Xaa at residue 7 is one Ser and Trp

<400> SEQUENCE: 6

Arg Ala Ser Gln Ser Ile Xaa Arg Trp Leu Ala
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Exemplified LCDR2
<220> FEATURE:
<221> NAME/KEY: MISC_FEATURE
<222> LOCATION: (7)..(7)
<223> OTHER INFORMATION: Xaa at residue 7 is one of Leu and Phe

<400> SEQUENCE: 7

His Asp Ala Ser Gln Leu Xaa Glu
1               5

<210> SEQ ID NO 8
<211> LENGTH: 9
<212> TYPE: PRT
<213> ORGANISM: Artificial Sequence
<220> FEATURE:
<223> OTHER INFORMATION: Exemplified LCDR3

<400> SEQUENCE: 8

Gln Gln Phe Asp Leu Leu Pro Leu Thr
1               5

<210> SEQ ID NO 9
<211> LENGTH: 123
<212> TYPE: PRT
<213> ORGANISM: Artificial Sequence
<220> FEATURE:
<223> OTHER INFORMATION: Exemplified HCVR
<220> FEATURE:
<221> NAME/KEY: MISC_FEATURE
<222> LOCATION: (62)..(62)
<223> OTHER INFORMATION: Xaa at residue 62 is one of Asp, Ala, Glu and
      Gln
<220> FEATURE:
<221> NAME/KEY: MISC_FEATURE
<222> LOCATION: (104)..(104)
<223> OTHER INFORMATION: Xaa at residue 104 is one of Asn and Thr
```

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Leu Ser Gly Gly Ser Thr Tyr Tyr Ala Xaa Ser His
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Val Gly Ala Ser Xaa His Asn Tyr Tyr Gly Met Asp Val
            100                 105                 110

Trp Gly Gln Gly Thr Met Val Thr Val Ser Ser
        115                 120
```

<210> SEQ ID NO 10
<211> LENGTH: 107
<212> TYPE: PRT
<213> ORGANISM: Artificial Sequence
<220> FEATURE:
<223> OTHER INFORMATION: Exemplified LCVR
<220> FEATURE:
<221> NAME/KEY: MISC_FEATURE
<222> LOCATION: (30)..(30)
<223> OTHER INFORMATION: Xaa at residue 30 is one of Ser and Trp
<220> FEATURE:
<221> NAME/KEY: MISC_FEATURE
<222> LOCATION: (55)..(55)
<223> OTHER INFORMATION: Xaa at residue 55 is one of Leu and Phe

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Xaa Arg Trp
            20                  25                  30

Leu Ala Trp Tyr Gln Gln Lys Pro Gly Lys Ala Pro Lys Leu Leu Ile
        35                  40                  45

His Asp Ala Ser Gln Leu Xaa Glu Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asp Leu Leu Pro Leu
                85                  90                  95

Thr Phe Gly Gly Gly Thr Lys Val Glu Ile Lys
            100                 105
```

<210> SEQ ID NO 11
<211> LENGTH: 1347
<212> TYPE: DNA
<213> ORGANISM: Artificial Sequence
<220> FEATURE:
<223> OTHER INFORMATION: Nucleotide Sequence Encoding HC of Exemplified
      Ab B

<400> SEQUENCE: 11

```
gaggtgcagc tgttggagtc tgggggaggc ttggtacagc ctggggggtc cctgagactc    60
```

| | |
|---|---|
| tcctgtgcag cctctggatt cacctttagc agctattaca tgagctgggt ccgccaggct | 120 |
| ccagggaagg gctggagtg gtctcagct attagtctga gtggtggtag cacatactac | 180 |
| gcagcgtccc acaagggccg gttcaccatc tccagagaca attccaagaa cacgctgtat | 240 |
| ctgcaaatga acagcctgag agccgaggac acggccgtat attactgtgt ccgggaggtg | 300 |
| ggagctagca ctcacaacta ctacggtatg gacgtctggg gccaagggac catggtcacc | 360 |
| gtctcttcag cttctaccaa gggcccatcg gtcttcccgc tagcgccctg ctccaggagc | 420 |
| acctccgaga gcacagccgc cctgggctgc ctggtcaagg actacttccc cgaaccggtg | 480 |
| acggtgtcgt ggaactcagg cgccctgacc agcggcgtgc acaccttccc ggctgtccta | 540 |
| cagtcctcag gactctactc cctcagcagc gtggtgaccg tgcctccag cagcttgggc | 600 |
| acgaagacct acacctgcaa cgtagatcac aagcccagca acaccaaggt ggacaagaga | 660 |
| gttgagtcca aatatggtcc cccatgccca ccctgcccag cacctgaggc cgccggggga | 720 |
| ccatcagtct tcctgttccc cccaaaaccc aaggacactc tcatgatctc ccggacccct | 780 |
| gaggtcacgt gcgtggtggt ggacgtgagc caggaagacc ccgaggtcca gttcaactgg | 840 |
| tacgtggatg gcgtggaggt gcataatgcc aagacaaagc cgcgggagga gcagttcaac | 900 |
| agcacgtacc gtgtggtcag cgtcctcacc gtcctgcacc aggactggct gaacggcaag | 960 |
| gagtacaagt gcaaggtctc caacaaaggc ctcccgtcct ccatcgagaa aaccatctcc | 1020 |
| aaagccaaag gcagccccg agagccacag gtgtacaccc tgcccccatc ccaggaggag | 1080 |
| atgaccaaga accaggtcag cctgacctgc ctggtcaaag gcttctaccc cagcgacatc | 1140 |
| gccgtggagt gggaaagcaa tgggcagccg gagaacaact acaagaccac gcctcccgtg | 1200 |
| ctggactccg acggctcctt cttcctctac agcaggctaa ccgtggacaa gagcaggtgg | 1260 |
| caggagggga atgtcttctc atgctccgtg atgcatgagg ctctgcacaa ccactacaca | 1320 |
| cagaagagcc tctccctgtc tctgggt | 1347 |

<210> SEQ ID NO 12
<211> LENGTH: 642
<212> TYPE: DNA
<213> ORGANISM: Artificial Sequence
<220> FEATURE:
<223> OTHER INFORMATION: Nucleotide Sequence Encoding LC of Exemplified Ab B

<400> SEQUENCE: 12

| | |
|---|---|
| gacatccaga tgacccagtc tccatcctcc ctgtctgcat ctgtaggaga cagagtcacc | 60 |
| atcacttgcc gggcgagtca gagtatttgg aggtggttgg cctggtatca gcagaaacca | 120 |
| gggaaagccc ctaagctcct gatccacgat gcatcccaat tgttcgaagg ggtcccatca | 180 |
| aggttcagtg gaagtggatc tgggacagat tttactttca ccatcagcag cctgcagcct | 240 |
| gaagatattg caacatatta ctgtcaacag tttgatttgc tccctctcac tttcggcgga | 300 |
| gggaccaagg tggagatcaa acggaccgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gc | 642 |

<210> SEQ ID NO 13

```
<211> LENGTH: 38
<212> TYPE: PRT
<213> ORGANISM: Artificial Sequence
<220> FEATURE:
<223> OTHER INFORMATION: Recombinant Human PACAP 38
<220> FEATURE:
<221> NAME/KEY: MOD_RES
<222> LOCATION: (38)..(38)
<223> OTHER INFORMATION: Lys at residue 38 is post-translationally
      modified by C-terminal amidation

<400> SEQUENCE: 13

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 14
<211> LENGTH: 27
<212> TYPE: PRT
<213> ORGANISM: Artificial Sequence
<220> FEATURE:
<223> OTHER INFORMATION: Recombinant Human PACAP27
<220> FEATURE:
<221> NAME/KEY: MOD_RES
<222> LOCATION: (27)..(27)
<223> OTHER INFORMATION: Leu at residue 27 is post-translationally
      modified by C-terminal amidation

<400> SEQUENCE: 14

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25
```

ANTI-PACAP ANTIBODY

REFERENCE TO AN ELECTRONIC SEQUENCE LISTING

The contents of the electronic sequence listing (X21602A SEQ LISTING.txt; Size: 15,135 bytes; and Date of Creation: Jan. 10, 2020) is herein incorporated by reference in its entirety.

The present invention is in the field of medicine. Particularly, the present invention relates to antibodies to pituitary adenylate cyclase-activating peptide (PACAP), compositions comprising such anti-PACAP antibodies, and methods of using such antibodies for the treatment of pain including primary headaches (including trigeminal autonomic cephalalgias), secondary headaches and migraines (including chronic migraine).

Pituitary adenylate cyclase-activating peptide (PACAP) is a neuropeptide distributed throughout the nervous system including the trigeminovascular system, trigeminal ganglia, spinal cord, hypothalamus, and pituitary. PACAP exists in at least two α-amidated active forms: PACAP38 (SEQ ID NO: 13), which comprises 38 amino acids and is the more prevalent active form, typically representing up to 90% of PACAP in mammalian tissue; and PACAP27 (SEQ ID NO: 14) which comprises the same 27 N-terminal amino acids as PACAP38. PACAP is believed to play roles in neuroprotection, neuromodulation, neurogenic inflammation and nociception and in causing pain, including headaches and migraines.

Headaches and migraines are estimated to impact 37 million patients a year, with more than two-thirds being untreated. Primary headache(s) is classified as headaches not resultant from a different or separate disease or disorder, while secondary headache(s) is classified as headaches resultant from a different or separate underlying cause (e.g., trauma, illness, or other disorder). Trigeminal autonornic cephalalgias ("TACs") are classified as primary headaches that include episodic and chronic cluster headache, paroxysmal hemicrania, hemicranias continua, and unilateral neuralgiform headache attacks. Migraine(s) refers to migraines "without aura" (formerly termed "common migraines") and "with aura" (formerly termed "classical migraines"). Chronic migraine(s) is classified as 15 or more headache days per month with at least eight of which are migraines. When migraine prevalence is two or more episodes per month, or when migraines significantly interfere with a patient's daily routine and/or acute medications are ineffective, physicians are encouraged to consider preventative treatment options. However, to date treatment options for migraine prophylaxis are often ineffective and current preventative and acute treatment options (e.g., antihypertensives, anticonvulsants, antidepressants) have low efficacy and associated disabling side effects.

The structure of PACAP is well-known in the art (see, for example, A. Miyata, A. et al., Biochem Biophys Res Comrnun 170: 643-648 (1990)) as are anti-PACAP antibodies. For example, U.S. Pat. No. 5,486,472A, International Patent Application Publication No. WO/2012/106407 A3, and U.S. Patent Application Publication No. 2016-304604 all disclose various anti-PACAP antibodies and potential uses thereof. However, to date, no antibody targeting PACAP has been approved for therapeutic use. Thus, there remains a need for alternative anti-PACAP antibodies. In particular, there remains a need for alternative anti-PACAP antibodies that neutralize PACAP with high potency, provide a sustained duration of action, and are capable of treating pain including primary and secondary headaches and migraines including chronic migraine. As with all therapeutic treatments, safety and toxicity remain a limitation and alternative anti-PACAP antibodies must not be attendant on unacceptable immunogenicity. There, thus, remains a need for alternative anti-PACAP antibodies which present a reduced risk of immunogenicity in humans. Such anti-PACAP antibodies will preferably also possess good physical-chemical properties to facilitate development, manufacturing, and formulation.

The present invention provides an antibody that binds human PACAP and which comprises a heavy chain variable region (HCVR) and a light chain variable region (LCVR), wherein the HCVR comprises the complementarity determining regions (CDRs) HCDR1, HCDR2 and HCDR3 and the LCVR comprises CDRs LCDR1, LCDR2 and LCDR3, wherein the amino acid sequence of HCDR1 is SEQ NO.3, the amino acid sequence of HCDR2 is SEQ ID NO.4, the amino acid sequence of HCDR3 is SEQ ID NO.5, the amino acid sequence of LCDR1 is SEQ ID NO.6, the amino acid sequence of LCDR2 is SEQ ID NO.7, and the amino acid sequence of LCDR3 is SEQ ID NO.8. In a particular embodiment HCDR2 comprises aspartic acid at residue 13, HCDR3 comprises asparagine at residue 8, LCDR1 comprises serine at residue 7, and LCDR2 comprises leucine at residue 7. In another particular embodiment, HCDR2 comprises alanine at residue 13, HCDR3 comprises threonine at residue 8, LCDR1 comprises tryptophan at residue 7, and LCDR2 comprises phenylalanine at residue 7. In a further particular embodiment, HCDR2 comprises glutamic acid at residue 13, HCDR3 comprises threonine at residue 8, LCDR1 comprises tryptophan at residue 7, and LCDR2 comprises phenylalanine at residue 7. In an even further particular embodiment, HCDR2 comprises glutamine at residue 13, HCDR3 comprises threonine at residue 8, LCDR1 comprises tryptophan at residue 7, and LCDR2 comprises phenylalanine at residue 7.

Embodiments of the present invention provide an antibody that binds human PACAP, comprising a HCVR and a LCVR, wherein the amino acid sequence of the HCVR is SEQ ID NO.9 and the amino acid sequence of the LCVR is SEQ ID NO. 10. In particular embodiments, HCVR comprises aspartic acid at residue 62 and asparagine at residue 104, and LCVR comprises serine at residue 30 and leucine at residue 55. In other particular embodiments, HCVR comprises alanine at residue 62 and threonine at residue 104, and LCVR comprises tryptophan at residue 30 and phenylalanine at residue 55. In some embodiments, HCVR comprises glutamic acid at residue 62 and threonine at residue 104, and LCVR comprises tryptophan at residue 30 and phenylalanine at residue 55. In some embodiments, HCVR comprises glutamine at residue 62 and threonine at residue 104, and LCVR comprises tryptophan at residue 30 and phenylalanine at residue 55.

In further embodiments, the present invention provides an antibody that binds human PACAP, comprising a heavy chain (HC) and a light chain (LC), wherein the amino acid sequence of the HC is SEQ ID NO.1 and the amino acid sequence of the LC is SEQ ID NO.2. In particular embodiments, HC comprises aspartic acid at residue 62, asparagine at residue 104, prolific at residue 231, alanine at residue 237 and alanine at residue 238, and LC comprises serine at residue 30 and leucine at residue 55. In other particular embodiments, HC comprises alanine at residue 62, threonine at residue 104, proline at residue 231, alanine at residue 237 and alanine at residue 238, and LC comprises tryptophan at residue 30 and phenylalanine at residue 55. In other particular embodiments HC comprises glutamic acid at residue 62, threonine at residue 104, proline at residue 231, alanine at residue 237 and alanine at residue 238, and LC comprises tryptophan at residue 30 and phenylalanine at residue 55. In some particular embodiments HC comprises glutamine at residue 62, threonine at residue 104, proline at residue 231, alanine at residue 237 and alanine at residue 238, and LC comprises tryptophan at residue 30 and phenylalanine at residue 55.

The present invention further provides pharmaceutical compositions comprising an antibody of the present invention and one or more pharmaceutically acceptable carriers, diluents or excipients. Further, the present invention provides a method of treating pain such as headaches, including primary and secondary headache comprising administering to a patient in need thereof a pharmaceutical composition of the present invention. In an even further embodiment, the primary headache is a TAC. In an even further embodiment, the present invention provides a method of treating migraines comprising administering to a patient in need thereof a pharmaceutical composition of the present invention. In some such embodiments, the migraine is chronic migraine. Further, the present invention provides a method of treating mast cell degranulation related pain comprising administering to a patient in need thereof an antibody or pharmaceutical composition of the present invention. According to some such embodiments mast cell degranulation related pain is one of primary or secondary headaches and migraine.

In addition, the present invention provides a method of treating pain such as primary headache, secondary headache and/or migraine comprising administering to a patient in need thereof an effective amount of an antibody of the present invention. According to some embodiments, the primary headache is a TAC. According to some embodiments, the migraine is chronic migraine.

The present invention also provides an antibody of the present invention for use in therapy. More particularly, the present invention provides an antibody of the present invention for use in treatment of pain. In particular embodiments, the present invention provides an antibody of the present invention for use in treatment of primary headache, secondary headache and/or migraine.

Further, the present invention provides the use of an antibody of the present invention in the manufacture of a medicament for the treatment of pain such as primary headache, secondary headache and/or migraine. In even more particular embodiments, the primary headache is a TAC. In some particular embodiments, the migraine is chronic migraine.

The present invention also relates to nucleic acid molecules and expression vectors encoding the antibodies of the present invention. In an embodiment, the present invention provides a DNA molecule comprising a polynucleotide sequence encoding a polypeptide having the amino acid sequence of SEQ ID NO.1, wherein residue 62 is aspartic acid, residue 104 is asparagine, residue 231 is proline, residue 237 is alanine and residue 238 is alanine. In some embodiments, residue 62 is alanine, residue 104 is threonine, residue 231 is proline, residue 237 is alanine and residue 238 is alanine. In some embodiments, residue 62 is glutamic acid, residue 104 is threonine, residue 231 is proline, residue 237 is alanine and residue 238 is alanine. In further embodiments, residue 62 is glutamine, residue 104 is threonine, residue 231 is proline, residue 237 is alanine and residue 238 is alanine Embodiments of the present invention also provide a DNA molecule comprising a polynucleotide sequence encoding a polypeptide having the amino acid sequence of SEQ ID NO.2, wherein residue 30 is serine and residue 55 is leucine. In some embodiments, residue 30 is tryptophan and residue 55 is phenylalanine.

In some embodiments, the DNA molecule of the present molecule comprises a polynucleotide sequence encoding a polypeptide having an amino acid sequence of SEQ ID NO.1 wherein residue 62 is aspartic acid, residue 104 is asparagine, residue 231 is proline, residue 237 is alanine and residue 238 is alanine, and comprising a polynucleotide sequence encoding a polypeptide having the amino acid sequence of SEQ ID NO. 2 wherein residue 30 is serine and residue 55 is leucine. In a particular embodiment the DNA molecule of the present molecule comprises a polynucleotide sequence encoding a polypeptide having an amino acid sequence of SEQ ID NO.1 wherein residue 62 is alanine, residue 104 is threonine, residue 231 is proline, residue 237 is alanine and residue 238 is alanine, and comprising a polynucleotide sequence encoding a polypeptide having the amino acid sequence of SEQ ID NO.2 wherein residue 30 is tryptophan and residue 55 is phenylalanine. In a particular embodiment the DNA molecule of the present molecule comprises a polynucleotide sequence encoding a polypeptide having an amino acid sequence of SEQ ID NO.1 wherein residue 62 is glutamic acid, residue 104 is threonine, residue 231 is proline, residue 237 is alanine and residue 238 is alanine, and comprising a polynucleotide sequence encoding a polypeptide having the amino acid sequence of SEQ ID NO.2 wherein residue 30 is tryptophan and residue 55 is phenylalanine. In another particular embodiment the DNA molecule of the present molecule comprises a polynucleotide sequence encoding a polypeptide having an amino acid sequence of SEQ ID NO.1 wherein residue 62 is glutamine, residue 104 is threonine, residue 231 is proline, residue 237 is alanine and residue 238 is alanine, and comprising a polynucleotide sequence encoding a polypeptide having the amino acid sequence of SEQ ID NO. 2 wherein residue 30 is tryptophan and residue 55 is phenylalanine. Further, the present invention provides an antibody prepared according to a process, wherein said process comprises cultivating a host cell comprising a polynucleotide sequence of the present invention, under conditions such that the antibody is expressed, and recovering from said host cell an antibody of the present invention.

As used herein, an "antibody" is an immunoglobulin molecule comprising 2 HCs and 2 LCs interconnected by disulfide bonds. The amino terminal portion of each LC and HC includes a variable region of about 100-120 amino acids primarily responsible for antigen recognition via the CDRs contained therein. The CDRs are interspersed with regions that are more conserved, termed framework regions ("FR"). Each LCVR and HCVR is composed of 3 CDRs and 4 FRs, arranged from amino-terminus to carboxy-terminus in the following order: FR1, CDR1, FR2, CDR2, FR3, CDR3, FR4. The 3 CDRs of the LC are referred to as "LCDR1, LCDR2, and LCDR3," and the 3 CDRs of the HC are referred to as "HCDR1, HCDR2, and HCDR3." The CDRs contain most of the residues which form specific interactions with the antigen. The functional ability of an antibody to bind a particular antigen is largely influenced by the six CDRs. Assignment of amino acids to CDR domains within the LCVR and HCVR regions of the antibodies of the present invention is based on the well-known Kabat numbering convention (Kabat, et al., *Ann. NY Acad. Set.* 190: 382-93 (1971); Kabat et al., *Sequences of Proteins of Immunological Interest*, Fifth Edition, U.S. Department of Health and Hunan Services, NIH Publication No. 91-3242 (1991)), and North numbering convention (North et al., A New Clustering of Antibody CDR Loop Conformations, Journal of Molecular Biology, 406:228-256 (2011)).

LCs are classified as kappa or lambda, which are each characterized by a particular constant region as known in the art. The antibodies of the present invention include kappa LCs. HCs are classified as gamma, mu, alpha, delta, or epsilon, and define the isotype of an antibody as IgG, IgM, IgA, IgD, or IgE, respectively. The antibodies of the present invention include IgG HCs. IgG antibodies can be further divided into subclasses, e.g., IgG1, IgG2, IgG3, IgG4. In a particular embodiment, the antibodies of the present invention are IgG4. The carboxy-terminal portion of each HC defines a constant region primarily responsible for effector function. In a particular embodiment, the antibodies of the present invention have one or more modifications in the constant region of each HC that reduces effector function. In a more particular embodiment, the antibodies of the present invention are IgG4 and have modifications in the constant region of both HCs that reduce effector function including the amino acid alanine at both residues 237 and 238 (residue numbering is linear and based on the exemplified HC of SEQ ID NO.1). In an even more particular embodiment, the antibodies of the present invention are IgG4 and have modifications in the constant region of both HCs that reduce effector function including the amino acid alanine at both residues 237 and 238 and have further modifications in the constant region of both HCs promoting stability including the amino acid proline at residue 231 (residue numbering is linear and based on the exemplified HC of SEQ ID NO.1).

The antibodies of the present invention are monoclonal antibodies ("mAbs"). mAbs can be produced, for example, by hybridoma technologies, recombinant technologies, phage display technologies, synthetic technologies, e.g., CDR-grafting, or combinations of such or other technologies known in the art. As referred to herein, mAbs are antibodies derived from a single copy or clone including, for example, any eukaryotic, prokaryotic or phage clone, and not the method by which it is produced.

Methods of producing and purifying antibodies are well known in the art. For example, a phage library can be screened, whereby thousands of Fab fragments are screened for interaction with recombinant human PACAP. Resulting interactions can be recovered, purified, and the amino acid sequences determined using conventional methods well known in the art, whereby initial lead antibodies can be constructed. The antibodies of the present invention are engineered to contain one or more human framework regions. Human framework germline sequences can be obtained from ImMunoGeneTics (INET) via their website, http://imgt.cines.fr, or from *The Immunoglobulin FactsBook* by Marie-Paule Lefranc and Gerard Lefranc, Academic Press, 2001, ISBN 012441351. According to particular embodiments, germline HC and LC framework regions for use in the antibodies of the present invention include 3-23 and O18, respectively.

In particular embodiments of the present invention, the antibody, or the nucleic acid encoding same, is provided in isolated form. As used herein, the term "isolated" refers to a protein, peptide, or nucleic acid which is free or substantially free from other macromolecular species found in a cellular environment.

The antibodies of the present invention may be prepared and purified using known methods. For example, cDNA sequences encoding a HC (for example the amino acid sequence given by SEQ ID NO.1) and a LC (for example, the amino acid sequence given by SEQ ID NO.2) may be cloned and engineered into a GS (glutamine synthetase) expression vector. The engineered immunoglobulin expression vector may then be stably transfected into CHO cells. As one of skill in the art will appreciate, mammalian expression of antibodies will result in glycosylation, typically at highly conserved N-glycosylation sites in the Fc region. Stable clones may be verified for expression of an antibody specifically binding to human PACAP. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

The antibodies of the present invention can be used in the treatment of patients. More particularly the antibodies of the present invention are expected to treat a class of pain, which specifically includes headache, both primary and secondary, and migraine including chronic migraine. Although antibodies of the present invention are expected to be useful in the treatment of pain, including primary and secondary headache and migraine, such antibodies may also be useful in the treatment of other pain. As used interchangeably herein, "treatment" and/or "treating" and/or "treat" are intended to refer to all processes wherein there may be a slowing, interrupting, arresting, controlling, stopping, or reversing of the progression of the disorders described herein, but does not necessarily indicate a total elimination of all disorder symptoms. Treatment includes administration of an antibody of the present invention for treatment of a disease or condition in a human that would benefit from a reduction in PACAP activity, and includes: (a) inhibiting further progression of the disease, i.e., arresting its development; (b) relieving the disease, i.e., causing regression of the disease or disorder or alleviating symptoms or complications thereof; and (c) preventing the onset of the disease of symptoms.

As used interchangeably herein, the term "patient," "subject," and "individual," refers to a human. In certain embodiments, the patient is further characterized with a disease, disorder, or condition (e.g., pain, for example primary or secondary headache and/or migraine including chronic migraine) that would benefit from a reduction in PACAP activity. In another embodiment, the patient is further characterized as being at risk of developing a condition described above, or condition that would benefit from a reduction in PACAP activity.

As used herein, the term "bind (or binds to)" refers to an interaction of an antibody with an epitope of human PACAP. The term "epitope" as used herein refers to discrete, three-dimensional sites of an antigen that are recognized by the antibodies of the present invention.

An antibody of the present invention can be incorporated into a pharmaceutical composition which can be prepared by methods well known in the art and comprise an antibody of the present invention and one or more pharmaceutically acceptable carrier(s) and/or diluent(s) (e.g., Remington, *The Science and Practice of Pharmacy*, 22$^{nd}$ Edition, Loyd V., Ed., Pharmaceutical Press, 2012, which provides a compendium of formulation techniques as are generally known to practitioners). Suitable carriers for pharmaceutical compositions include any material which, when combined with the antibody of the present invention, retains the molecule's activity and is non-reactive with the patient's immune system.

A pharmaceutical composition comprising an antibody of the present invention can be administered to a patient at risk for, or exhibiting, diseases or disorders as described herein by parental routes (e.g., subcutaneous, intravenous, intraperitoneal, intramuscular, or transdermal). A pharmaceutical composition of the present invention contains an "effective" or "therapeutically effective" amount, as used interchangeably herein, of an antibody of the present invention. An effective amount refers to an amount necessary (at dosages and for periods of time and for the means of administration) to achieve the desired therapeutic result. An effective amount of the antibody may vary according to factors such as the disease state, age, sex, and weight of the individual, and the ability of the antibody to elicit a desired response in the individual. An effective amount is also one in which any toxic or detrimental effects of the antibody of the present invention are outweighed by the therapeutically beneficial effects.

EXAMPLES

Example 1. Engineering and Expression of Exemplified Anti-PACAP Antibodies

Significant problems associated with chemical and physical stability were encountered when constructing an anti-PACAP antibody of the present invention. For example, problems encountered with initial humanized constructs include low binding affinity, unacceptable immunogenicity, variable region deamidation, oxidation, isomerization and low potency.

Chemical and physical modifications were therefore engineered to improve the binding affinity, eliminate or reduce HC dimerization, reduce immunogenicity, and improve chemical and physical stability of the antibodies of the present invention. Amino acid modifications were engineered throughout both the heavy and light chains. Extensive protein stability studies were also performed and the constructed antibodies were screened for expression and thermostability properties as well as other properties including binding affinity. The following antibodies, which include numerous modifications from original constructs, are identified as possessing high binding affinity, being chemically and physically stabile, possessing low immunogenicity and possessing pharmacokinetic properties consistent with monthly administration. None of the modifications comprising the antibodies of the present invention were identified in initially humanized constructs.

Exemplified anti-PACAP antibodies of the present invention are presented in Table 1. The exemplified antibodies include heavy chains of SEQ ID NO: 1 and light chains of SEQ ID NO: 2 as well as human HC framework 3-23 and human kappa LCs with framework O18. Additionally, engineered modifications within both the light and heavy chains which improve chemical and physical stability as well as functional properties of the antibodies are provided in Table 1. The relationship of the various regions of the exemplified anti-PACAP antibodies is as follows (numbering of amino acids applies linear numbering; assignment of amino acids to variable domains is based on the International Immunogenetics Information System® available at www.imgt.org; assignment of amino acids to CDR domains is based on the well-known North numbering convention, with the exception of HCDR2 which is based on the well-known Kabat numbering convention).

TABLE 1

Amino acid regions of exemplified anti-PACAP antibodies of the present invention.

| SEQ ID NO: 1 | | | SEQ ID NO: 2 | | |
|---|---|---|---|---|---|
| HCVR | Region | Positions | LCVR | Region | Positions |
| | FRH1 | 1-22 | | FRL1 | 1-23 |
| | HCDR1 | 23-35 | | LCDRI | 24-34 |
| | FRH2 | 36-49 | | FRL2 | 35-48 |
| | HCDR2 | 50-66 | | LCDR2 | 49-56 |
| | FRH3 | 67-96 | | FRL3 | 57-88 |
| | HCDR3 | 97-112 | | LCDR3 | 89-97 |
| | FRH4 | 113-123 | | FRL4 | 98-107 |
| Constant | CH | 124-449 | Constant | CL | 108-214 |
| Exemplified Ab A | 62D; 104N; 231P; 237A; 238A | | Exemplified Ab A | 30S; 55L | |
| Exemplified Ab B | 62A; 104T; 231P; 237A; 238A | | Exemplified Ab B | 30W; 55F | |
| Exemplified Ab C | 62E; 104T; 231P; 237A; 238A | | Exemplified Ab C | 30W; 55F | |
| Exemplified Ab D | 62Q; 104T; 231P; 237A; 238A | | Exemplified Ab D | 30W; 55F | |

The following Examples and assays demonstrate that the antibodies of the present invention are useful for treating pain including primary and secondary headache and migraine. It should be understood however, that the following Examples are set forth by way of illustration and not limitation, and that various modifications may be made by one of ordinary skill in the art.

The exemplified anti-PACAP antibodies of the present invention can be expressed and purified essentially as follows. A glutamine synthetase (GS) expression vector containing a DNA sequence encoding a HC amino acid sequence according to Table 1 (for example, a DNA sequence of SEQ NO:11 encoding a HC of Exemplified Antibody B presented in Table 1) and a DNA sequence encoding a LC amino acid sequence according to Table 1 (for example, a DNA sequence of SEQ ID NO:12 encoding a LC of Exemplified Antibody B presented in Table 1) is used to transfect a Chinese hamster ovary cell line (CHO) by electroporation. The expression vector encodes an SV Early (Simian Virus 40E) promoter and the gene for GS. Expression of GS allows for the biochemical synthesis of glutamine, an amino acid required by the CHO cells. Post-transfection, cells undergo bulk selection with 50 μM L-methionine sulfoxitnine (MSX). The inhibition of GS by MSX is utilized to increase the stringency of selection. Cells with integration of the expression vector cDNA into transcriptionally active regions of the host cell genome can be selected against CHO wild type cells, which express an endogenous level of GS. Transfected pools are plated at low density to allow for close-to-clonal outgrowth of stable expressing cells. The masterwells are screened for antibody expression and then scaled up in serum-free, suspension cultures to be used for production. Clarified medium, into which the antibody has been secreted, is applied to a Protein A affinity column that has been equilibrated with a compatible buffer, such as phosphate buffered saline (pH 7.4). The column is washed with 1M NaCl to remove nonspecific binding components. Bound antibody is eluted, for example, with sodium citrate at pH (approx.) 3.5 and fractions are neutralized with 1M Tris buffer. Antibody fractions are detected, such as by SDS-PAGE or analytical size-exclusion, and then are pooled. Soluble aggregate and multimers may be effectively removed by common techniques, including size exclusion, hydrophobic interaction, ion exchange, or hydroxyapatite chromatography. Exemplified anti-PACAP antibody of the present invention is concentrated and/or sterile filtered using common techniques. The purity of exemplified antibody after these chromatography steps is greater than 95%. Exemplified anti-PACAP antibody of the present invention may be immediately frozen at −70° C. or stored at 4° C. for several months.

Example 2. Binding Affinity

Binding affinity ($K_D$) for each antibody-antigen complex is determined using a kinetic exclusion 96-well plate-based assay (adapted from Estep et al., mAbs, 2013, 5:270-278). Briefly, a 3-fold dilution series for each Exemplified Ab (set forth in Table 1) is prepared from a starting concentration of 7290 pM to 41 fM; each series including an antibody-blank control. Samples are prepared in 3% (w/v) Blocker A solution (MSD, #R93AA-1) and a fixed final antigen concentration of 30 pM of N-terminal biotinylated PACAP27 (custom synthesis, CPC Scientific) or N-terminal biotinylated PACAP38 (Anaspec, #23590) is added to each sample. A volume of 100 µl of each antigen-antibody sample is added to individual wells of a 96-well microtiter plate (Greiner, EK-20101) in duplicate. The plate is sealed with optical adhesive film (Thermo Fisher Scientific, #4311971) and incubated at 37° C. for 3 to 4 days to allow for sample equilibrium. On the day before analysis, each row of a 96-well MSD Standard plate (MSD, #L15XA) is coated with 30 µl of the corresponding antibody (as used in the titration series) at a concentration of 3 µg/ml in phosphate buffered saline (PBS). On the day of the experiment, the MSD Standard plate is washed once with 150 µl PBS and blocked with 150 µl of 3% Blocker A solution for 45 min at 30° C. with shaking at 300 rpm on a MaxQ 4450 benchtop shaker (Thermo Fisher Scientific). Following three washes with PBS, 50 µl of each antigen-antibody sample (prepared and incubated as described above) is added to the MSD Standard plate and incubated for 150 seconds at 30° C. with shaking at 300 rpm. Following a single wash with PBS, 50 µl of 1 µg/ml SULFO-TAG labeled Streptavidin (MSD, #R32AD-5) prepared in 1% (w/v) Blocker A solution is added and the MSD Standard plate and the plate is incubated at 30° C. for 3 minutes with shaking at 300 rpm. The plate is washed three more times with PBS followed by the addition of 1.50 µl/well of 1× Read buffer (MSD, #R92TC-2). The MSD Standard plate is read using a MESO Quickplex SQ 120/1300 instrument (Meso Scale Discovery). Data analysis is done using SigmaPlot (Version 12.5, Systat Software) and binding affinity ($K_D$) is determined using SigmaPlot's integrated Four Parameter Logistic Curve Model. Results are provided in Table 2.

TABLE 2

Binding affinity ($K_D$) of antibody-antigen complexes at 37° C.

| | Binding Affinity, $K_D$ (pM, 37° C.) | |
| --- | --- | --- |
| Antibody | Antigen (PACAP38) | Antigen (PACAP27) |
| Exemplified Ab A | not determined | 37.0 |
| Exemplified Ab B | 12.8 | 11.6 |
| Exemplified Ab C | 14.6 | 14.5 |
| Exemplified Ab D | 9.0 | 10.5 |

Example 3. In Vivo PACAP Degradation

Degradation of circulating PACAP38, in vivo, is assessed in rats. One of control IgG4 antibody (10 mg/kg) or Exemplified Antibody A (10 mg/kg) is injected into rats intravenously. Baseline PACAP38, in plasma, is assessed for each rat and then rats are injected, intravenously, with 6 µg/kg PACAP38. Following PACAP38 injection, plasma samples are collected over a 120 minute period and total levels of PACAP38 (bound or unbound to antibody) are determined via a modified ELISA format. Briefly, a 96 well MSD plate (MSD, catalog #: L15xA-1) is coated with 30 µl/well of 1 ug/ml anti-PACAP38 antibody (US Biological Cat # P1775-03C) in PBS and incubated overnight at 40° C. The plate is washed three times with 200 µl/well PBST followed by blocking with 150 µl/well 3% Blocker A (MSD Cat # R93BA-2) in PBS at room temperature for 1 hour with rotation at 650 rpm. Thereafter, the plate is washed three times with 200 µl/well PBST. Calibrator of PACAP38 (Bachem Cat # H430-0500) is diluted at 1000 pg/mL with Assay Buffer containing one part diluent 2 (MSD Cat # R51-BB-3) and thirty-nine parts diluent 3 (MSD Cat # R51BA-3) supplemented with 200 µg/ml HBR1 (Scantibodies Cat # 3KC533) and 10 µg/ml of Biotin-Exemplified Antibody A. Calibrator standard curve is prepared by three-fold serial dilution of 1000 pg/mL calibrator with Assay Buffer. Plasma samples are diluted 40 fold in diluent 3 supplemented with 200 µg/mL HBR1 and 10 µg/mL of Biotin-Exemplified Antibody A. 25 µl of different concentrations of calibrator and diluted plasma samples are added to individual wells of the assay plate and incubated at room temperature for 2 hours with rotation at 650 rpm, After washing the plate 3 times with 200 µl/well PBST, 25 µl of 0.5 µg/ml Sulfo-tag labeled goat anti-human IgG (MSD Cat # R32AJ-1) in diluent 3 is added to each well and the plate is incubated at room temperature for 1 hour. Plates are then washed three times with 200 µl/well PBST and 150 µl of 2× read buffer T (MSD, Cat # R92TC-3) is added to each well and signal is read with a MSD plate reader (results, presented as detectable PACAP38 levels, mean±SEM (n=2-3)). Results are presented in Table 3.

TABLE 3

PACAP38 plasma levels

PACAP38 Plasma Levels (ng/mL) at time points post PACAP38 injection (mean ± SEM (N))

| Antibody | baseline | 5 mins. | 30 mins. | 60 mins. | 90 mins. | 120 mins. |
|---|---|---|---|---|---|---|
| Exemplified Ab A | 0.4 ± 0.0 (2) | 200.0 + 23.0 (3) | 74.1 ± 11.8 (3) | 37.8 ± 3.2 (3) | 20.7 ± 2.9 (3) | 11.7 ± 2.5 (2) |
| Control IgG4 Ab | 0.5 ± 0.5 (3) | 6.2 ± 2.5 (3) | 2.3 ± 0.9 (3) | 1.1 ± 0.3 (3) | 0.5 ± 0.2 (3) | 0.3 ± 0.1 (3) |

Results presented in Table 3 demonstrate Exemplified Antibody A prevents PACAP38 distribution upon intravenous injection but does not prevent PACAP38 in vivo degradation.

Example 4. Inhibition of PACAP27, PACAP38, or VIP-induced cAMP

Neutralization of PACAP27, PACAP38, and VIP induced cAMP stimulation, by the antibodies of the present invention, is assessed in CHO-K1 cells (ATCC, catalog #CCL-61) transfected with vectors expressing either human PAC 1 (NP_001186564.1) or human VPAC2 (NP_003373.2). CHO-K1 cells are harvested with nonenzymatic. Cell Dissociation Buffer (Gibco #313131-014), counted, centrifigured and resuspended in assay buffer to 10,000 cells/25 µl. Concentrated cells (10,000 in 25 µl) are added to wells of a 96-well plate.

Exemplified Antibodies (set forth in Table 1) are serial diluted in 100 µl assay buffer (HBSS with calcium and magnesium (Hyclone, ThermoScientific, SH30268), 0.1% BSA (Sigma-Aldrich, #A7888), 500 µM IBMX (Sigma-Aldrich, 15879)), to 4-times desired final concentration. Diluted Exemplified Antibodies are incubated with agonist (at 2× the final concentration) for 15 minutes at room temperature. Final concentrations of agonist: 100 pM for PACAP27 and PACAP38 in the human PAC1, 800 pM PACAP27 and PACAP38 in the human VPAC2, 800 pM VIP in the human VPAC2 assays. Thereafter, 25 µl of Exemplified Antibody-agonist solution is added to individual wells of the 96-well plate (containing cells) and incubated for 1 hour at room temperature. cAMP formation in each well is determined using cAMP femto to 2 (Cisbio, 62AM5PEC). 25 µl cAMP-d2 working solution (Cisbio, 62AM5PEC) is added to each well followed by the addition of 25 µl Anti cAMP-Cryptate working solution and the plate is incubated for 1 hr at room temperature in the dark, Resulting HTRF signal is measured at 665 and 620 nm using an Envision 12 (Perkin Elmer, excitation 330 nm) instrument, and the ratio of 665/620 is plotted to quantify cAMP (data are plotted using Graphpad Prism 7 and IC50 values are determined using the integrated Four Parameter Logistic Curve Model fitting routines). Results are provided in Table 4 as mean±SEM.

TABLE 4

In Vitro Neutralization of PACAP27 and PACAP38 Induced cAMP Increase

Inhibition (IC50) (pM, mean ± SEM (N))

| Antibody | PACAP38 (100 pM) in hPAC1 | PACAP27 (100 pM) in hPAC1 | PACAP38 (800 pM) in hVPAC2 | PACAP27 (800 pM) in hVPAC2 | VIP (800 pM) in hVPAC2 |
|---|---|---|---|---|---|
| Exemplified Ab A | 554 ± 264 (N = 2) | 2250 (N = 1) | 714 ± 194 (N = 6) | 781 ± 340 (N = 2) | >100,000 (N = 1) |
| Exemplified Ab B | 265 ± 62 (N = 3) | 270 ± 103 (N = 2) | 294 ± 60 (N = 3) | 605 ± 135 (N = 2) | >100,000 (N = 1) |
| Exemplified Ab C | 303 ± 15 (N = 3) | 311 ± 29 (N = 2) | 325 ± 99 (N = 3) | 595 ± 219 (N = 2) | >100,000 (N = 1) |
| Exemplified Ab D | 205 ± 35 (N = 3) | 212 ± 42 (N = 2) | 243 ± 112 (N = 3) | 515 ± 127 (N = 2) | >100,000 (N = 1) |

Example 5. Immunogenicity Analysis

Immunogenicity assessment, in silico, is performed with EpiMatrix T-cell epitope prediction software (within the Interactive Screening and Protein Reengineering Interface (ISPRI) web-based portal (Epivax, Inc.)) including Tregitope-adjusted Epimatrix Scores. Light chain variable region (LCVR) and heavy chain variable region (HCVR) protein sequences associated with each antibody are separately analyzed. According to Epivax, protein sequences with Tregitope-adjusted Epimatrix scores greater than zero have a higher overall immunogenic potential. EpiMatrix Cluster Immunogenicity assessment is also performed for each LCVR and HCVR to identify T-cell epitope clusters within the CDR of each antibody. The presence of T-cell epitope clusters, as defined by the presence of 2 or more adjacent EpiBars, is associated with a higher overall immunogenic potential. Using the North CDR definition, no CDR-related T-cell epitope clusters are identified in Exemplified Antibodies A, B, or C. A T-cell Epitope cluster of 4 adjacent EpiBars is identified in CDR2 of the LCVR of comparator antibody ALD (described as "Ab 1.H" in U.S. Patent Publication Number US 2016/0304604) indicating that the comparator antibody has higher immunogenic potential. Results are provided in Tables 5A, 5B and 5C.

TABLE 5A

In Silico immunogenicity risk assessment via EpiMatrix T-cell Epitope Prediction

| | Epimatrix Score | | |
|---|---|---|---|
| Antibody | HCVR | LCVR | HCVR + LCVR |
| Exemplified Ab A | 58.84 | 19.44 | 40.61 |

TABLE 5A-continued

In Silico immunogenicity risk assessment via EpiMatrix T-cell Epitope Prediction

| Antibody | Epimatrix Score | | |
|---|---|---|---|
| | HCVR | LCVR | HCVR + LCVR |
| Exemplified Ab B | 65.12 | 26.41 | 47.21 |
| Exemplified Ab C | 58.74 | 26.41 | 43.79 |
| Exemplified Ab D | 65.49 | 26.41 | 47.41 |
| ALD 1.H | 70.11 | 35.2 | 53.16 |

TABLE 5B

Tregitope-Adjusted Epimatrix Assessment

| Antibody | Tregitope-Adjusted Epimatrix Score | | |
|---|---|---|---|
| | HCVR | LCVR | HCVR + LCVR |
| Exemplified Ab A | −32.82 | −34.22 | −33.46 |
| Exemplified Ab B | −26.54 | −27.24 | −26.86 |
| Exemplified Ab C | −32.92 | −27.24 | −30.29 |
| Exemplified Ab D | −26.17 | −27.24 | −26.67 |
| ALD 1.H | −28.41 | 1.41 | −13.93 |

TABLE 5C

In Silico immunogenicity risk assessment via EpiMatrix Cluster Immunogenicity assessment

| Antibody | CDR-related Epibar Clusters |
|---|---|
| Exemplified Ab A | 0 |
| Exemplified Ab B | 0 |
| Exemplified Ab C | 0 |
| Exemplified Ab D | 0 |
| ALD 1.H | 1 |

Example 6. Neutralization of Mast Cell Degranulation-Induced PACAP Release

Human mast cells are differentiated in culture from human cord blood stem cells using StemSpan Media (StemCell) and SCF/IL-6. On the day of the assay, mast cells are plated at 100,000 cells per 50 into wells of a 96-well tissue culture plate in Tyrode's buffer (130 mM NaCl, 5 mM KCl, 1.4 mM CaCl2, 1 mM MgCl2, 5.6 mM glucose, 10 mM HEPES and 0.1% BSA, pH 7.4). Cells are treated with PACAP38 or PACAP27 in the presence or absence of an Exemplified Antibody as described below.

Single point tests are carried out by adding 25 µl of 4×-concentrated Exemplified Antibody per well (final concentration of 153 µM Exemplified Antibody). Dose curve tests are carried out by adding 25 µl of 4×-concentrated antibody per well for a final dose range of 0 to 153 µM (three-fold dilutions). 25 µl of 4×-concentrated PACAP38 or PACAP27 is added to each well to a final concentration 1 µM PACAP (38 or 27). Assay medium only is used as a no treatment control and IgG4 mAb is used as a negative control. Testing is done in triplicate. The 96-well plates are placed in an incubator (37° C.) for 30 minutes. Following incubation, 30 µl/well of supernatant are collected and tryptase activity is measured by commercial assay (Millipore). Percent (%) tryptase release in supernatant is calculated by the following equation: ((Experimental tryptase release—vehicle control tryptase release)/(total tryptase release—vehicle control tryptase release)×100, where total tryptase release is obtained by freeze/thawing mast cells). Results are provided in Tables 6A, 6B and 6C.

TABLE 6A

Single Point Inhibition of PACAP (27 and 38) Induced Tryptase Release in Human Mast Cells

| Antibody | Percentage Tryptase Release upon addition of PACAP38 or 27 (%) | |
|---|---|---|
| | PACAP38 | PACAP27 |
| Exemplified Ab B | 4.9 ± 1.1 | 21 ± 1.4 |
| Exemplified Ab C | 5.5 ± 1.4 | 14.2 ± 1.1 |
| Exemplified Ab D | 4.2 ± 0.7 | 15.1 ± 4.0 |
| Assay Medium only | −0.3 ± 0.3 | −0.3 ± 0.3 |
| IgG4 mAb | 103.6 ± 0.5 | 109.7 ± 0.4 |

TABLE 6B

Dose Curve Inhibition of PACAP27 Induced Tryptase Release in Human Mast Cells

| Antibody | Dose (uM) | Percentage Tryptase Release upon addition of PACAP27 (%) |
|---|---|---|
| Exemplified Ab B | 153 | 10.3 ± 0.9 |
| | 51 | 19.4 ± 6.4 |
| | 17 | 11.6 ± 7.1 |
| | 5.6 | 8.1 ± 2.9 |
| | 1.8 | 11.7 ± 1.6 |
| | 0.6 | 54.0 ± 2.0 |
| | 0.2 | 78.1 ± 1.0 |
| | 0 | 85.2 ± 3.4 |
| Exemplified Ab C | 153 | 9.7 ± 2.3 |
| | 51 | 17.8 ± 2.3 |
| | 17 | 8.0 ± 0.6 |
| | 5.6 | 11.5 ± 4.9 |
| | 1.8 | 10.4 ± 2.6 |
| | 0.6 | 55.4 ± 6.0 |
| | 0.2 | 85.2 ± 1.6 |
| | 0 | 85.8 ± 4.8 |
| Exemplified Ab D | 153 | 9.4 ± 0.8 |
| | 51 | 26.0 ± 6.3 |
| | 17 | 19.8 ± 3.4 |
| | 5.6 | 16.4 ± 10.8 |
| | 1.8 | 20.3 ± 8.4 |
| | 0.6 | 73.0 ± 2.1 |
| | 0.2 | 86.5 ± 1.8 |
| | 0 | 92.7 ± 1.5 |
| Assay Medium only | | −0.2 ± 1.0 |
| IgG4 mAb | 153 | 94.8 ± 4.8 |

TABLE 6C

Dose Curve Inhibition of PACAP38 Induced Tryptase Release in Human Mast Cells

| Antibody | Dose (uM) | Percentage Tryptase Release upon addition of PACAP38 (%) |
|---|---|---|
| Exemplified Ab B | 153 | 2.0 ± 0.3 |
| | 51 | 14.6 ± 2.1 |
| | 17 | 14.9 ± 2.6 |

TABLE 6C-continued

Dose Curve Inhibition of PACAP38 Induced
Tryptase Release in Human Mast Cells

| Antibody | Dose (uM) | Percentage Tryptase Release upon addition of PACAP38 (%) |
|---|---|---|
|  | 5.6 | 22.0 ± 4.1 |
|  | 1.8 | 25.2 ± 1.4 |
|  | 0.6 | 52.4 ± 9.3 |
|  | 0.2 | 73.7 ± 1.3 |
|  | 0 | 77.2 ± 1.0 |
| Exemplified Ab C | 153 | 2.8 ± 0.3 |
|  | 51 | 12.1 ± 2.3 |
|  | 17 | 15.5 ± 0.9 |
|  | 5.6 | 21.9 ± 3.8 |
|  | 1.8 | 26.5 ± 4.3 |
|  | 0.6 | 66.6 ± 1.0 |
|  | 0.2 | 77.6 ± 0.3 |
|  | 0 | 80.3 ± 2.6 |
| Exemplified Ab D | 153 | 1.7 ± 0.1 |
|  | 51 | 14.7 ± 1.5 |
|  | 17 | 19.6 ± 3.6 |
|  | 5.6 | 25.9 ± 6.2 |
|  | 1.8 | 31.3 ± 3.8 |
|  | 0.6 | 64.5 ± 4.1 |
|  | 0.2 | 74.0 ± 1.8 |
|  | 0 | 76.5 ± 0.7 |
| Assay Medium only |  | −0.2 ± 1.0 |
| IgG4 mAb | 153 | 79.6 ± 4.1 |

Example 7. In Vivo PACAP-Induced cAMP Neutralization

Neutralization of PACAP-induced plasma cAMP increase, in vivo, is assessed in CD-1 murine model (Envigo). Briefly, male CD-1 mice are subcutaneously administered 10 mg/kg of one of: Control IgG4 antibody (N=6); Control IgG4 antibody plus PBS/rolipram only (N=5); Exemplified Antibody B (N=5); Exemplified Antibody C (N=5); or Exemplified Antibody D (N=6). Three days-post antibody treatment, mice are intravenously administered PACAP38 (13 nmols/kg) plus rolipram (100 ug/mL); some mice previously treated with IgG4 control antibody are intravenously administer PBS (containing 0.2% ethanol, 1% BSA, 5 ml/kg, and rolipram (100 µg/ml) only. Ten minutes post-PACAP38 treatment, blood is collected in EDTA containing tubes and plasma is separated by centrifugation. Plasma levels of cAMP are determined using commercially available cAMP ELISA (Cell Bios, Inc.) according to manufacturer instructions. Statistical analysis applies log transformed cAMP concentration in a one-way ANOVA (Graphpad Prism 7) followed by Dunnett's post hoc analysis. Results are set forth in Table 7 as mean±SE.

TABLE 7

PACAP-Induced Plasma cAMP Levels

| Antibody | Plasma cAMP levels (nM, mean ± SEM) |
|---|---|
| IgG4 Control Ab (plus PBS/rolipram only) | 238 ± 60 (N = 5) * |
| IgG4 Control Ab (plus PACAP) | 4095 ± 318 (N = 6) |
| Exemplified Ab B (plus PACAP) | 715 ± 60 (N = 5) * |
| Exemplified Ab C (plus PACAP) | 666 ± 96 (N = 5) * |
| Exemplified Ab D (plus PACAP) | 560 ± 130 (N = 6) * |

* p < 0.0001 vs IgG4 Control Ab (PACAP38)

Example 8. Neutralization of Trigeminal Ganglia Stimulation-Induced Dural Plasma Protein Extravasation In Vivo The ability of anti-PACAP antibodies of the present invention to block, in vivo, plasma protein extravasation induced by release of PACAP following stimulation of the trigeminal ganglia is examined using a rat model. Briefly, Sprague-Dawley rats (Envigo, males, 250-350 g) are subcutaneously administered one of 1-10 mg/kg of Exemplified Antibody A; 3-30 mg/kg of Exemplified Antibody B; or 3 or 10 mg/kg of Control IgG4 Ab. Seventy-two hours later, rats are anesthetized with Nembutal (65 mg/kg, iv.) and placed in a stereotaxic frame (David Kopf Instruments) with the incisor bar set at −2.5 mm. A mid-line sagittal scalp incision is made, followed by two pairs of bilateral holes drilled through the skull (3.2 mm posteriorly, 1.8 and 3.8 mm laterally, all coordinates referenced to bregma). Pairs of stainless steel stimulating electrodes (Rhodes Medical Systems, Inc.) are lowered through the holes in both hemispheres to a depth of 9.2 mm from the dura. Two-minutes prior to trigeminal ganglion stimulation, fluorescein isothiocyanate-labeled bovine serum albumin (FITC-BSA) (20 mg/kg, iv.), a marker for protein extravasation, is injected into the femoral vein. The left trigeminal ganglion is stimulated for 5 minutes at a current intensity of 1.0 mA (5 Hz, 5 msec pulse duration) with a Model S48 Grass Instrument Stimulator with PSIU6 photoelectric isolation unit (Grass-Telefactor). Five minutes following stimulation, the rats are sacrificed by exsanguination with 40 ml of saline.

Following sacrifice of the rats, the top of the skull is removed and dural membrane is collected. Membrane samples are removed from both hemispheres, rinsed with water, and spread flat on microscope slides. Slides are dried for 15 minutes on a slide warmer and tissues are cover-slipped with a 70% glycerol/water solution. A fluorescence microscope (Zeiss) equipped with a grating monochromator and a spectrophotometer are used to quantify FITC-BSA dye in each dural sample. The extravasation induced by electrical stimulation of the trigeminal ganglion is an ipsilateral effect (i.e. occurs only on the side of the dura in which the trigeminal ganglion is stimulated), thus allowing the unstimulated half of the dura to serve as a control. The ratio of extravasation in the dura from the stimulated side versus the unstimulated side is calculated. Results are provided in Table 8 (mean±SE).

TABLE 8

Trigeminal Ganglia Stimulation-Induced Dural Plasma Protein Extravasation

| Antibody (mg/kg) | Extravasation Ratio (mean ± SEM) |
|---|---|
| IgG4 Control Ab (10 mg/kg) (N = 3) | 1.87 ± 0.04 |
| Exemplified Ab A (1 mg/kg) (N = 3) | 1.93 ± 0.04 |
| Exemplified Ab A (3 mg/kg) (N = 3) | 1.59 ± 0.07 |
| Exemplified Ab A (10 mg/kg) (N = 3) | 1.13 ± 0.05 |
| IgG4 Control Ab (3 mg/kg) (N = 3) | 1.82 ± 0.02 |
| IgG4 Control Ab (10 mg/kg) N = 3) | 1.90 ± 0.04 |
| IgG4 Control Ab (30 mg/kg) N = 3) | 1.95 ± 0.05 |
| Exemplified Ab B (3 mg/kg) (N = 3) | 1.83 ± 0.06 |
| Exemplified Ab B (10 mg/kg) (N = 3) | 1.21 ± 0.06 |
| Exemplified Ab B (30 mg/kg) (N = 3) | 1.07 ± 0.04 |

Example 9. Pharmacokinetics of Exemplified Anti-PACAP Antibodies

Serum pharmacokinetics of exemplified antibodies of the present invention are characterized in male cynomolgus monkeys (n=2) following a single SC administration by total IgG assay. Animals are injected subcutaneous with Exemplified Antibody B (10 mg/kg) and serum samples collected at 1, 3, 6, 24, 48, 72, 96, 120, 144, 168, 240, 336, 504 and 672 hours post injection. Total IgG assay is performed generally as described herein. Briefly, 100 uL/well of 1 ug/mL goat anti-human IgG F(ab')₂ antibody (Jackson ImmunoResearch Laboratories, Inc., Catalog Number 109-006-097) is coated on an Immulon 4HBX plate. Wells are incubated with one of standards (a standard curve for Exemplified Antibody B is prepared from 15.63-1,000 ng/mL), control or serum samples, followed by 100 ul/well of 1:10,000 diluted mouse anti-human IgG Fc-horseradish peroxidase (FIRP; SouthernBiotech, Catalog Number 9040-05) for detection. Unbound detection reagent is washed away. Thereafter, 100 ul/well TMB Microwell Peroxidase Substrate System is added to the wells. Color development is stopped by addition of 100 ul/well TMB Stop Solution and optical density is measured at 450 nm with wavelength correction set to 630 nm. Immunoreactivity is determined from known amounts of Exemplified Antibody B in 100% cynomolgus monkey serum, followed by a minimum required dilution of 1:10 in Blocker™ Casein in PBS using a 5-parameter algorithm (StatLia; version 3.2). Following procedures essentially as described above, apparent clearance (CL/F) of 0.49 mL/hr/kg, apparent volume of distribution (V/F) of 114.0 mL/kg, and terminal half-life of 171 hours calculated by non-compartmental analysis are calculated for Exemplified Antibody B. The pharmacokinetic results obtained are consistent with therapeutic antibodies capable of extended duration of action.

SEQUENCES

Exemplified HC
(SEQ ID NO. 1)
EVQLLESGGGLVQPGGSLRLSCAASGFTFSSYYMSWVRQAPGKGLEWVSA

ISLSGGSTYYAXSHKGRFTISRDNSKNTLYLQMNSLRAEDTAVYYCVREV

GASXHNYYGMDVWGQGTMVTVSSASTKGPSVFPLAPCSRSTSESTAALGC

LVKDYFPEPVTVSWNSGALTSGVHTFPAVLQSSGLYSLSSVVTVPSSSLG

TKTYTCNVDHKPSNTKVDKRVESKYGPPCPXCPAPEXXGGPSVFLFPPKP

KDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLG wherein, X at residue 62 is one of D, A, E and Q; X at residue 104 is one of N and T; X at residue 231 is one of P and S; X at residue 237 is one of A and F; and X at residue 238 is one of A and L.

Exemplified LC
(SEQ ID NO. 2)
DIQMTQSPSSLSASVGDRVTITCRASQSIXRWLAWYQQKPGKAPKLLIHD

ASQLXEGVPSRFSGSGSGTDFTFTISSLQPEDIATYYCQQFDLLPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC wherein X at residue 30 is one of S and W; and X at residue 55 is one of L and F.

Exemplified HCDR1
(SEQ ID NO. 3)
AASGFTFSSYYMS

Exemplified HCDR2
(SEQ ID NO. 4)
AISLSGGSTYYAXSHKG wherein X at residue 13 is one of D, A, E and Q.

Exemplified HCDR3
(SEQ ID NO. 5)
VREVGASXHNYYGMDV wherein X at residue 8 is one of N and T.

Exemplified LCDR1
(SEQ ID NO. 6)
RASQSIXRWLA wherein X at residue 7 is one of S and W.

Exemplified LCDR2
(SEQ ID NO. 7)
HDASQLXE wherein X at residue 7 is one of L and F.

Exemplified LCDR3
(SEQ ID NO. 8)
QQFDLLPLT

Exemplified HCVR
(SEQ ID NO. 9)
EVQLLESGGGLVQPGGSLRLSCAASGFTFSSYYMSWVRQAPGKGLEWVSA

ISLSGGSTYYAXSHKGRFTISRDNSKNTLYLQMNSLRAEDTAVYYCVREV

GASXHNYYGMDVWGQGTMVTVSS wherein, X at residue 62 is one of D, A, E and Q; and X at residue 104 is one of N and Exemplified LCVR
(SEQ ID NO. 10)
DIQMTQSPSSLSASVGDRVTITCRASQSIXRWLAWYQQKPGKAPKILIHD

ASQLXEGVPSRFSGSGSGTDFTFTISSLQPEDIATYWQQFDLLPLTFGGG

TKVEIK wherein X at residue 30 is one of S and W; and X at residue 55 is one of L and F.

Nucleotide Scuuence Encoding HC of Exemplified Ab B (SEQ ID NO. 11)

gaggtgcagctgttggagtctgggggaggc ttggtacagcctggggggtccctgagactc tcctgtgcagcctctggattcacctttagc agctattacatgagctgggtccgccaggct ccagggaaggggctggagtgggtctcagct attagtctgagtggtggtaacacatactac gcagcgtcccacaagggccggttcaccatc tccagagacaattccaagaacacgctgtat ctgcaaatgaacagcctgagagccgaggac acagccgtatattactgtgtccaggaggta ggagctagcactcacaactactacggtatg gacgtctggggccaagggaccatggtcacc gtctcttcagcttctaccaagggcccatcg gtcttcccgctagcaccctgctccaggagc acctccgagagcacagccgccctgggctgc ctggtcaaggactacttccccgaaccggtg acgatgtcgtggaactcaggcgccctgacc agcggcgtgcacaccttcccaactatccta cagtcctcaggactctactccctcagcagc gtggtgaccgtgccctccagcagcttgggc acgaagacctacacctacaacgtagatcac aagcccagcaacaccaaggtggacaagaga gttgagtccaaatatggtcccccatgccca ccctgcccagcacctgaggccgccggggga ccatcagtcttcctgttcccccaaaaccc aaggacactctcatgatctcccggacccct gaggtcacgtgcgtggtggtggacgtgagc caggaagaccccgaggtccagttcaactgg tacgtggatggcgtggaggtgcataatgcc aagacaaagccgcgggaggagcagttcaac agcacgtaccgtgtggtcagcgtcctcacc gtcctgcaccaggactggctgaacggcaag gagtacaagtgcaaggtctccaacaaaggc ctcccgtcctccatcgagaaaaccatctcc aaagccaaagggcagccccgagagccacag gtgtacaccctgcccccatcccaggaggag atgaccaagaaccaggtcagcctgacctgc ctggtcaaaggcttctaccccagcgacatc gccgtggagtgggaaagcaatgggcagccg gagaacaactacaagaccacgcctcccgtg ctggactccgacggctccttcttcctctac agcaggctaaccgtggacaagagcaggtgg caggaggggaatgtcttctcatgctccgtg atgcatgaggctctgcacaaccactacaca cagaagagcactccctgtctctgggt Nucleotide Sequence Encoding LC of Exemplified Ab B (SEQ ID NO. 12)

gacatccagatgacccagtctccatcctcc ctgtctgcatctgtaggagacagagtcacc atcacttgccgggcgagtcagagtatttgg aggtggttggcctggtatcagcagaaacca aggaaagcccctaagctcctgatccacgat gcatcccaattgttcgaaggggtcccatca aggttcagtggaagtggatctgggacagat tttactttcaccatcagcagcctgcagcct gaagatattgcaacatattactgtcaacag tttgatttgctccctctcactttcggcgga gggaccaaggtggagatcaaacggaccgtg gctgcaccatctgtcttcatcttcccgcca tctgatgagcagttgaaatctggaactgcc tctgttgtgtgcctgctgaataacttctat cccagagaggccaaagtacagtggaaggtg gataacgccctccaatcgggtaactcccag gagagtgtcacagagcaggacagcaaggac agcacctacagcctcagcagcaccctgacg -continued

```
ctgagcaaagcagactacgagaaacacaaa gtctacgcctgcgaagtcacccatcagggc ctgagctcgcccgtcacaaagagcttcaac aggggagagtgc
```

Amino Acid Sequence of Recombinant Human PACAP 38
(SEQ ID NO. 13)

HSDGIFTDSYSRYRKQMAVKKYLAAVLGKRYKQRVKNK wherein K at residue 38 is post-translational modified by C-terminal amidation Amino Acid Sequence of Recombinant Human PACAP 27
(SEQ ID NO. 14)

HSDGIFTDSYSRYRKQMAVKKYLAAVL wherein L at residue 27 is post-translationally modified by C-terminal amidation

---

We claim:

1. A pharmaceutical composition comprising:
    an antibody that binds human pituitary adenylate cyclase-activating peptide comprising a heavy chain variable region (HCVR) and a light chain variable region (LCVR), wherein the HCVR comprises complementarity determining regions (CDRs) HCDR1, HCDR2, and HCDR3 and the LCVR comprises CDRs LCDR1, LCDR2, and LCDR3, wherein the amino acid sequence of HCDR1 is SEQ ID NO.3, the amino acid sequence of HCDR2 is SEQ ID NO.4, the amino acid sequence of HCDR3 is SEQ ID NO.5, the amino acid sequence of LCDR1 is SEQ ID NO.6, the amino acid sequence of LCDR2 is SEQ ID NO.7, and the amino acid sequence of LCDR3 is SEQ ID NO.8, wherein HCDR2 comprises aspartic acid, alanine, glutamic acid or glutamine at residue 13 of SEQ ID NO. 4, HCDR3 comprises asparagine or threonine at residue 8 of SEQ ID NO. 5, LCDR1 comprises serine or tryptophan at residue 7 of SEQ ID NO. 6, LCDR2 comprises leucine or phenylalanine at residue 7 of SEQ ID NO. 7; and one or more pharmaceutically acceptable carriers, diluents or excipients.

2. The pharmaceutical composition of claim 1, wherein HCDR2 comprises aspartic acid at residue 13; HCDR3 comprises asparagine at residue 8; LCDR1 comprises serine at residue 7; and LCDR2 comprises leucine at residue 7.

3. The pharmaceutical composition of claim 1, wherein HCDR2 comprises alanine at residue 13; HCDR3 comprises threonine at residue 8; LCDR1 comprises tryptophan at residue 7; and LCDR2 comprises phenylalanine at residue 7.

4. The pharmaceutical composition of claim 1, wherein HCDR2 comprises glutamic acid at residue 13; HCDR3 comprises threonine at residue 8; LCDR1 comprises tryptophan at residue 7; and LCDR2 comprises phenylalanine at residue 7.

5. The pharmaceutical composition of claim 1, wherein HCDR2 comprises glutamine at residue 13; HCDR3 comprises threonine at residue 8; LCDR1 comprises tryptophan at residue 7; and LCDR2 comprises phenylalanine at residue 7.

6. The pharmaceutical composition of claim 1, comprising a heavy chain variable region (HCVR) and a light chain variable region (LCVR), wherein the amino acid sequence of the HCVR is SEQ ID NO.9 and the amino acid sequence of the LCVR is SEQ ID NO. 10.

7. The pharmaceutical composition of claim 6, wherein HCVR comprises aspartic acid at residue 62 and asparagine at residue 104, and wherein LCVR comprises serine at residue 30 and leucine at residue 55.

8. The pharmaceutical composition of claim 6, wherein HCVR comprises alanine at residue 62 and threonine at residue 104, and wherein LCVR comprises tryptophan at residue 30 and phenylalanine at residue 55.

9. The pharmaceutical composition of claim 6, wherein HCVR comprises glutamic acid at residue 62 and threonine at residue 104, and wherein LCVR comprises tryptophan at residue 30 and phenylalanine at residue 55.

10. The pharmaceutical composition of claim 6, wherein HCVR comprises glutamine at residue 62 and threonine at residue 104, and wherein LCVR comprises tryptophan at residue 30 and phenylalanine at residue 55.

11. A pharmaceutical composition comprising an antibody that binds human pituitary adenylate cyclase-activating peptide comprising a heavy chain (HC) and a light chain (LC), wherein the amino acid sequence of the HC is SEQ ID NO: 1 and the amino acid sequence of the LC is SEQ ID NO: 2, wherein HC comprises aspartic acid, alanine, glutamic acid or glutamine at residue 62 and asparagine or threonine at residue 104 of SEQ ID NO: 1 and wherein LC comprises serine or tryptophan at residue 30 and leucine or phenylalanine at residue 55 of SEQ ID NO: 2; and one or more pharmaceutically acceptable carriers, diluents or excipients.

12. The pharmaceutical composition of claim 11, wherein HC comprises aspartic acid at residue 62, asparagine at residue 104, proline at residue 231, alanine at residue 237 and alanine at residue 238, and wherein LC comprises serine at residue 30 and leucine at residue 55.

13. The pharmaceutical composition of claim 11, wherein HC comprises alanine at residue 62, threonine at residue 104, proline at residue 231, alanine at residue 237 and alanine at residue 238, and wherein LC comprises tryptophan at residue 30 and phenylalanine at residue 55.

14. The pharmaceutical composition of claim 11, wherein HC comprises glutamic acid at residue 62, threonine at residue 104, proline at residue 231, alanine at residue 237 and alanine at residue 238, and wherein LC comprises tryptophan at residue 30 and phenylalanine at residue 55.

15. The pharmaceutical composition of claim 11, wherein HC comprises glutamine at residue 62, threonine at residue 104, proline at residue 231, alanine at residue 237 and alanine at residue 238, and wherein LC comprises tryptophan at residue 30 and phenylalanine at residue 55.

16. A method of treating a primary headache, secondary headache or migraine comprising administering to a patient in need thereof an effective amount of a pharmaceutical composition of claim 1.

17. The method of claim 16, wherein the primary headache is a trigeminal autonomic cephalalgias.

18. The method of claim 17, wherein the trigeminal autonomic cephalalgias is one of episodic cluster headache, chronic cluster headache, paroxysmal hemicranias, and unilateral neuralgiform headache attack.

* * * * *